US009468586B2

(12) United States Patent
Kvale

(10) Patent No.: US 9,468,586 B2
(45) Date of Patent: Oct. 18, 2016

(54) PIERCE AND FILL DEVICE

(71) Applicant: GE HEALTHCARE LIMITED, Buckinghamshire (GB)

(72) Inventor: Svein Kvale, Oslo (NO)

(73) Assignee: GE HEALTHCARE LIMITED, Buckinghamshire (GB)

(*) Notice: Subject to any disclaimer, the term of this patent is extended or adjusted under 35 U.S.C. 154(b) by 349 days.

(21) Appl. No.: 14/352,140

(22) PCT Filed: Oct. 28, 2012

(86) PCT No.: PCT/US2012/062346
§ 371 (c)(1),
(2) Date: Apr. 16, 2014

(87) PCT Pub. No.: WO2013/066779
PCT Pub. Date: May 10, 2013

(65) Prior Publication Data

US 2014/0238542 A1 Aug. 28, 2014

Related U.S. Application Data

(60) Provisional application No. 61/553,550, filed on Oct. 31, 2011.

(51) Int. Cl.

| | |
|---|---|
| ***A61B 19/00*** | (2006.01) |
| ***A61J 1/14*** | (2006.01) |
| ***A61J 1/20*** | (2006.01) |
| ***B65D 83/00*** | (2006.01) |
| ***B65B 3/00*** | (2006.01) |

(52) U.S. Cl.
CPC ............ *A61J 1/1406* (2013.01); *A61J 1/1412* (2013.01); *A61J 1/1475* (2013.01); *A61J 1/20* (2013.01); *B65B 3/003* (2013.01); *B65D 83/00* (2013.01); *A61J 1/1425* (2015.05); *A61J 1/2075* (2015.05)

(58) Field of Classification Search
CPC ........ A61J 1/20; A61J 1/1406; A61J 1/1412; A61J 1/1425; A61J 1/1475
See application file for complete search history.

(56) References Cited

U.S. PATENT DOCUMENTS

| | | | |
|---|---|---|---|
| 3,807,467 | A | 4/1974 | Tascher et al. |
| 5,232,029 | A | 8/1993 | Knox et al. |

(Continued)

FOREIGN PATENT DOCUMENTS

| | | | |
|---|---|---|---|
| CN | 101983158 | A | 3/2011 |
| EP | 2389969 | A1 | 11/2011 |
| EP | 2391329 | A1 | 12/2011 |
| EP | 2049062 | B1 | 6/2013 |

(Continued)

OTHER PUBLICATIONS

EP Office Action, dated Mar. 9, 2015; 5 pages.

*Primary Examiner* — Leslie Deak

(57) ABSTRACT

A pierce and fill connector cap for a vial sealed by an elastomeric septum includes a vial collar and a needle holder. The vial collar body defines a collar aperture to be positioned in overlying registry with the septum of the vial, and the needle holder includes a needle holder body providing a means for holding a pair of elongate needles in registry with the collar aperture. The needle holder body holds at least one needle therein in a bent or deflected orientation and is moveable with respect to the vial collar between a first position spaced from the vial collar and a second position proximate the vial collar, such that the needled held by the needle holder will puncture through the vial septum.

20 Claims, 5 Drawing Sheets

(56) References Cited

U.S. PATENT DOCUMENTS

| | | | |
|---|---|---|---|
| 6,209,738 | B1 | 4/2001 | Jansen et al. |
| 8,562,582 | B2 | 10/2013 | Tuckwell et al. |
| 9,278,181 | B2 | 3/2016 | Meron et al. |
| 9,402,784 | B2 | 8/2016 | Simpson et al. |
| 2011/0030845 | A1 | 2/2011 | Chong |
| 2011/0094619 | A1 | 4/2011 | Steel et al. |
| 2012/0053554 | A1 | 3/2012 | Simpson et al. |

FOREIGN PATENT DOCUMENTS

| | | | |
|---|---|---|---|
| JP | 48-005709 | B1 | 2/1973 |
| JP | 2-68854 | U | 3/1990 |
| JP | 2009-538123 | A | 11/2009 |
| JP | 5819396 | B2 | 11/2015 |
| JP | 5917152 | B2 | 5/2016 |
| WO | 2007140238 | A2 | 12/2007 |
| WO | 2009100428 | A1 | 8/2009 |
| WO | 2010085870 | A1 | 8/2010 |
| WO | 2011-117867 | A2 | 9/2011 |

PIERCE AND FILL DEVICE

This application is a filing under 35 U.S.C. 371 of international application number PCT/US2012/062346, filed Oct. 28, 2012, which claims priority to U.S. application No. 61/553,550 filed Oct. 31, 2011, the entire disclosure of which is hereby incorporated by reference.

FIELD OF THE INVENTION

The present invention relates to the field of dispense and fill devices. More specifically, the present invention is directed to a piercing device for a fluid container which allows piercing of a container stopper or septum while the container is still within a container or bag so as to maintain the sterility of the fluidpath of a dispenser for filling the container.

BACKGROUND OF THE INVENTION

For most dispensing solutions of a Positron Emission Tomography (PET) tracer, a bulk tracer solution needs to be divided into several fractions. Such dispensing needs to be done under aseptic conditions, typically Class A clean room with class B background. The operations for these PET tracers, as the tracers are radioactive, are desirably conducted in a fully-automated manner within shielded cells.

Most PET tracer manufacturing sites have limited number of hot-cells with class A clean room environment. Therefore a means enabling aseptic filling in class C environment would expand the potential PET production sites that could produce the tracers. Additionally, enabling any PET tracer manufacturing site to dispense in aseptic condition within a clean room class C may be the basis for a new dispenser to be provided to a wider market (beyond tracer production centers having clean room dispensing facilities).

WO2009/100428 discloses a way to dispense aseptically fluids in a closed sterile disposable fluid path (called disposable kit) allowing thus this operation to be performed in a clean room class C whilst dispensing is usually performed in clean room class A environment. Within the disposable kit, the connection between the closed sterile vial and the fluid path is ensured by a needle piercing the vial stopper.

A pre-piercing of the stopper during assembly of the disposable kit in the factory may not be an appropriate solution for sterile connection. Indeed aging of the assembly between the time the kit was assembled and the time it is used for dispensing may lead to leaks at the piercing holes, thus compromising sterility of the connection.

There is therefore a need in the art for a means of connecting a dispense vial to a dispense cassette closer to the time of dispense cassette use. There is also a need in the art for a means of connecting the dispense vial to the dispense cassette while both are still within a container or bag maintaining a sterile environment for the surfaces which will conduct a pharmaceutical product.

There is also a need for a ready to use 4-vial dispenser kit. Redesign of the clam shell can be done so that the stoppers can be pierced by the needles prior to use without opening the protecting bags that serve as a sterility barrier.

DETAILED DESCRIPTION OF THE PREFERRED EMBODIMENTS

Figure 1:
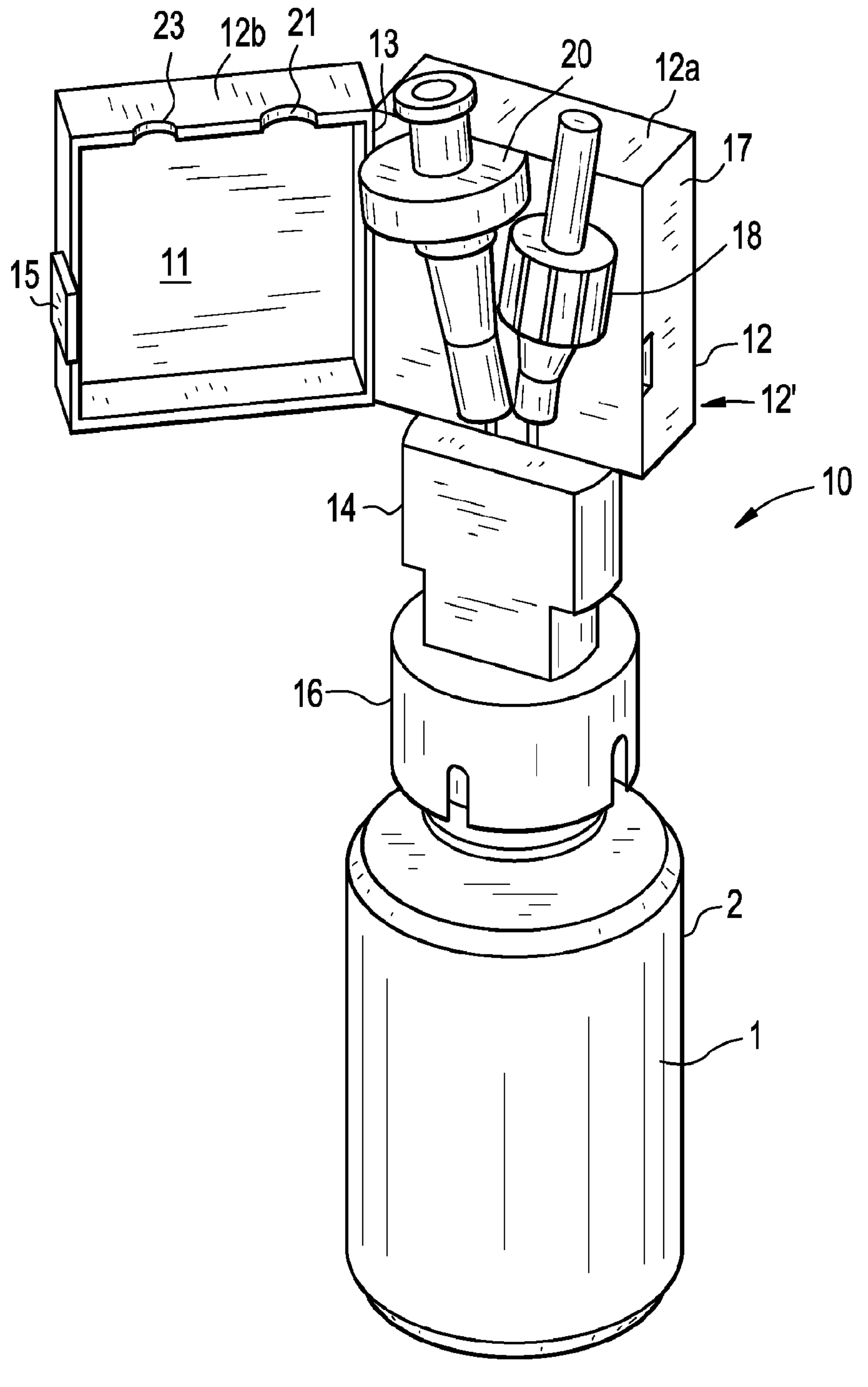
FIG. 1 depicts a piercing device of the present invention, showing the piercing device in the piercing configuration (i.e., extended towards the vial), with the support block shown open so as to show the positioning of the fill needle and the vent therein.
Figure 4:
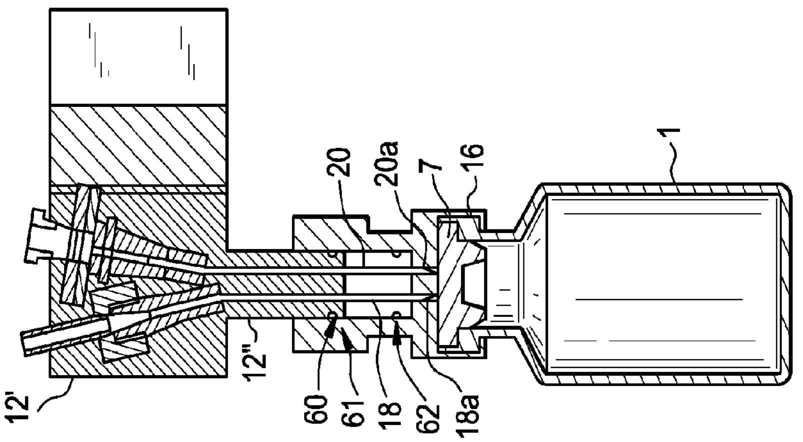
FIG. 4 depicts a cross-sectional view of the piercing device of FIG. 3 taken through the line 4-4 of FIG. 3.
Figure 3:
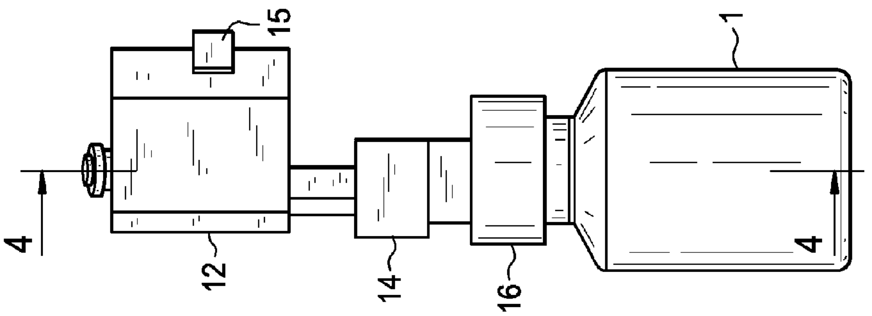
FIG. 3 depicts a side elevational view of the piercing device FIG. 2.

In view of the needs of the prior art, the present invention discloses a device and method for connecting a dispense needle of a sterile dispense cassette and a closed sterile vial just before use, desirably while both items are still sterile in a plastic bag or container. The tips of dispense needle and a vent needle may be provided in close proximity to each other by providing a piercing device which bends them at an angle about their mid-portions. The sharpened portions of both the dispense and vent needle may be provided essentially parallel to each other while the physically larger opposing ends, which support the connectors and filters of the needles, may be deflected away from each other.

The sharpened tips of the needles may thus be held close to the center of the septum to be pierced but far enough away from each other so as to form their own distinct puncture in the septum, so as to minimize coring or flaking of the septum material. Thus, while each needle will separately penetrate the septum, there will be sufficient material around each to ensure proper sealing about each needle so as to avoid undesired leakage about the needles (as could occur should the needles form a single puncture of the septum). Additionally, the present invention provides that both the dispense and vent needles will penetrate the septum at about a 90-degree angle. Moreover, the present invention supports the two needles during spiking and fixes both the vent housing and the tubing connection to the dispense (or fill) needle. The present invention, called a "connector cap" or a "piercing device" allows one or more needles to pierce a stopper of a closed sterile vial in a safe manner while still inside a sterile bag. The device will allow the operator to pierce the stopper just before opening the sterile bag, ensuring therefore the piercing in sterile condition and also keeping the leak-tightness properties of the stopper as it may thus be pierced only minutes before its usage.

The present invention may be used with a vial hermetically-closed (with an elastomeric stopper or septum) and includes a connector cap (or piercing device) containing one or more needles maintained on the top of the vial in overlying registry with the septum. The piercing device of the present invention is desirably formed of a polymeric material suitable for dispensing radioactive pharmaceutical fluids. When accommodating two needles in the connector cap, one of the needles supports a sterile gas 0.22 μm liquid filter (to filter the incoming liquid, e.g. the drug product) on a second end thereof, the other needle, when gas venting is required, supports a sterile 0.22 μm gas filter (filter used to vent the vial). The two filters may be connected directly onto the snap-and pierce cap or may be part of the fluid path (tubes, stopcock manifolds, etc.) connected to the snap-and-pierce cap. Typically, the 0.22 μm sterile gas filter is directly connected to the snap-and-pierce cap (or at least in direct fluid communication with the vial cavity) while the 0.22 μm liquid filter is part of the fluidpath connected to the snap-and-pierce cap (i.e. the filter is connected to the stopcock manifold part of the disposable dispensing kit).

All items are sterilized and sealed within a bag to ensure sterile storage. To connect the vial to the filters, the connector cap is positioned over the stopper of the vial so as to enable penetration of the needles into the vial through its stopper. This operation is desirably performed while all items are still in the sterile bag. The bag may further include a plastic tray holding each component in formed depressions and which includes a deflectable blister for each cap of the present invention so as to facilitate this operation.

Thus the whole kit is assembled, then inserted in a plastic bag, suitable for sterile packaging, then sealed in appropriate clean room class and then sterilized (e.g. sterilization through gamma irradiation but other sterilization means may also be used). The septum on the vial remains unpierced until the operator on dispensing site punches the needles through the stoppers while the whole dispensing kit is still in the sealed plastic bag. Because the disposable dispensing kit and the piercing device is inside the plastic bag, this operation is performed in an aseptic environment no matter what class environment the operator is in.

Once this connection is made, i.e., once the device is actuated to pierce the septum of the associated vial, the bag can be opened without compromising sterility of the vial as inlet and outlet are protected through 0.22 μm filters.

The present invention provides a connector cap for a vial sealed by an elastomeric septum. The connector cap includes a vial collar having a vial collar body defining a collar aperture to be positioned in overlying registry with the septum of the vial. The connector cap further includes a needle holder comprising a needle holder body having a first portion providing a means for engaging the first end of an elongate needle in registry with the collar aperture and a second portion for securing an opposed second end of the needle. The needle holder body is moveable with respect to the vial collar between a first position spaced from said vial collar and a second position proximate the vial collar, such that the free end of the first portion of a needle held by the needle holder will puncture through the vial septum, wherein the first and second portions of the needle holder body cause a needle held thereby to be bent between the first and second ends of the needle.

The dispensing device, or cassette, may consist in several vials equipped with the pierce and snap cap and a system allowing all of the connector caps to pierce their respective vials prior to opening the container in which they are provided.

The piercing device of the present invention will allow an operator to pierce the vials without opening the protecting bags. The piercing device provides a good support for the collar to be able to push the vial against the collar.

The needle with the luer connector and the needle with vent filter fixed in the collar to prevent that the needles is pushed out of the collar during spiking.

The needle is desirably perpendicular to the stopper in order to provide good spiking. The needle is forced to have a bend of about 10 degrees in order to have the needles parallel and perpendicular to the stopper while also deflecting their filter and connection portions clear of each other.

The collar is divided into two parts, one that holds the needles and another that ensure that needles are aligned before spiking.

The upper part of the collar holds the needles with the vent filter and luer connection with the tubing. The needles with the vent filter and luer connection are put into the upper part which is then fixed into position by the spring force of the metal of the needle. There is a lid that is closing to ensure that the needles are not falling out during transport and spiking. The lid is held in place so as to further clamp the dispense and vent needles to the base portion of the needle holder.

The spiking is performed by pushing the vial towards the needle holder. The vial collar and vial slide towards the needle holder and the spiking is performed. This is desirably done manually by the operator with the use of finger force.

The needle holder of the piercing device may be removed in the hot cell to release the vials.

The needles have two separated channels in the lower portion of the needle holder which prevent the needles from penetrating the stopper at the same spot which could lead to a leakage around the needle since there will not be stopper rubber sealing around the needle.

The present invention may thus provide a four vial dispensing fluid-path that does not require aseptic connections to be made in a cleanroom, but allows these connections to be made at the user site, just prior to removing the fluid path from the bag/container.

Referring to FIGS. 1-6, the present invention provides a piercing device 10 for penetrating a sealed container 1 at the appropriate time prior to filling the container. Container 1 includes a vial body 2 defining a vial cavity 3 and having an upstanding annular neck 4 and an outwardly-protruding annular rim 5. Annular neck 4 defines a vial aperture 6 in open fluid communication with vial cavity 3. An elastomeric septum 7 spans across aperture 6 so as to seal cavity 3 from the outside environment. Septum 7 may be adhered to vial neck by any conventional means such as by compatible adhesives or by interference fit with neck 4 either about rim 5 or within aperture 6 (as per a vial stopper). Container 1 may further include an annular metallic crimp for mechanically securing septum 7 across aperture 6. The crimp would include a central aperture in open overlying registry with septum 7 so as to expose septum 7 for piercing by one or more needles for filling into and/or dispensing from cavity 3.

As shown in FIG. 1, piercing device 10 includes a needle holder 12, a piercing guide 14, and a vial collar 16. Needle holder 12 maintains the needles in place and enables connection to the filters and the fluidpath (filters may be directly connected to the needle holder or be part of the fluidpath connected to the needle holder) to piercing device 10. Piercing guide 14 and needle holder 12 desirably include cooperative detents 60 and 61, respectively, to hold the needles away from the stopper until needle holder 12 is moved to the second position, guided to proper septum piercing by guide 14. Piercing guide 14 includes a second detent 62 that allows detent 61 of needle holder 12 to pass thereby as it is extended to the second position, but then resists retraction of detent 61 therepast so as to maintain needle holder 12 at the second position. Vial collar 16 ensures piercing device 10 is tightly connected onto the top of the sterile vial. Needle holder 12 is shown with a fill needle 18 and a vent needle 20 fixed to extend in overlying registry with septum 7 of container 1. In a first position, needle holder 12 maintains needles 18 and 20 in spaced separation from septum 7. Needle holder 12 includes a lower portion that may be moved along, i.e., within, piercing guide 14 to a second position, such that the free ends 18*a* and 20*a* of needles 18 and 20 pierce through septum 7 so as to extend into cavity 3 of container 1. Each of needles 18 and 20 typically include elongate cannulas 22 and 24 supported by a base luer 26 and 28, respectively.

Needle holder 12 is designed to bend or deflect needles 18 and 20 radially-outward from the elongate axis of the needle holder body. Needles 18 and 20 may be inserted into a lower portion 12" of needle holder 12 in an undeflected orientation and then bent radially-outward to a deflected orientation which needle holder 12 is then able to maintain the needles in. Forces are applied at the free ends of the needles and at the hubs, as well as at a central location therebetween, so as to cause the deflection of the needles. The upper portion 12' will then hold or clamp the needles securely in the deflected orientation. By 'deflected orientation', the present invention contemplates that the passageway through the hub will no longer be linearly-aligned with the passageway of the needle at its free end. The bending or deflection of the needle will thus occur along some portion between the free end of the needle and the hub.

Figure 2:
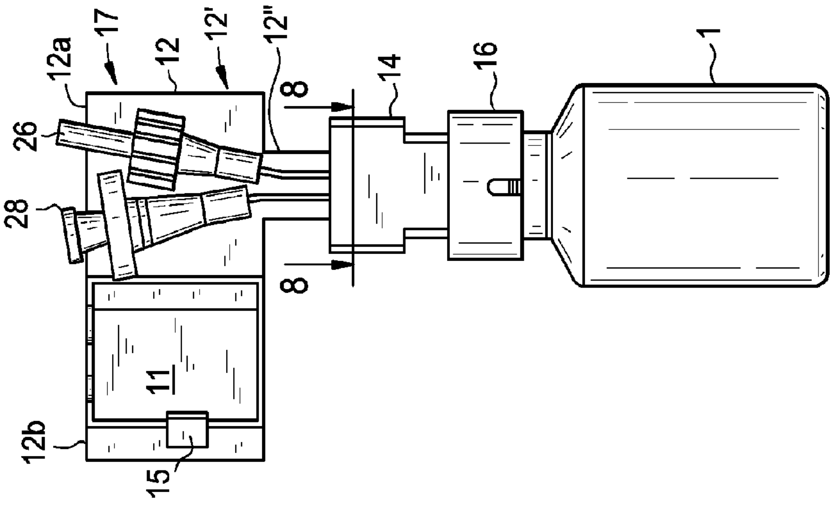
FIG. 2 depicts a front elevational view of the piercing device of FIG. 1, shown in the shipping configuration with the support block in a raised position with respect to the collar and vial.
Figure 6:
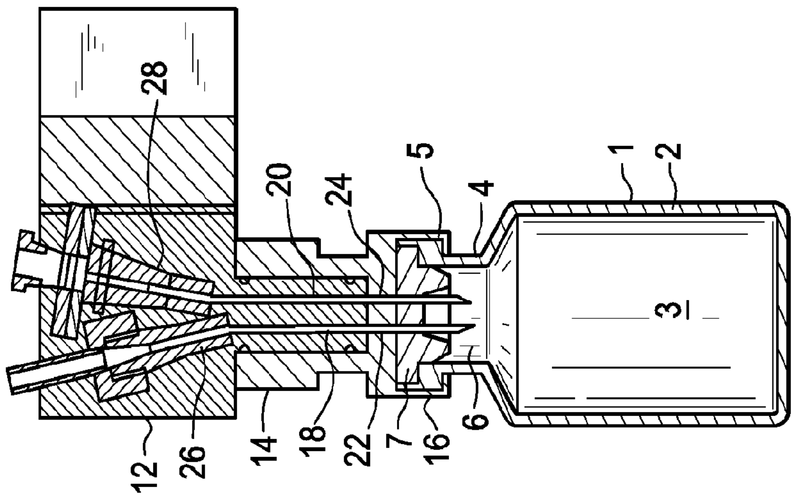
FIG. 6 depicts a cross-sectional view of the piercing device of the present invention, taken through the line 6-6 of FIG. 5.
Figure 5:
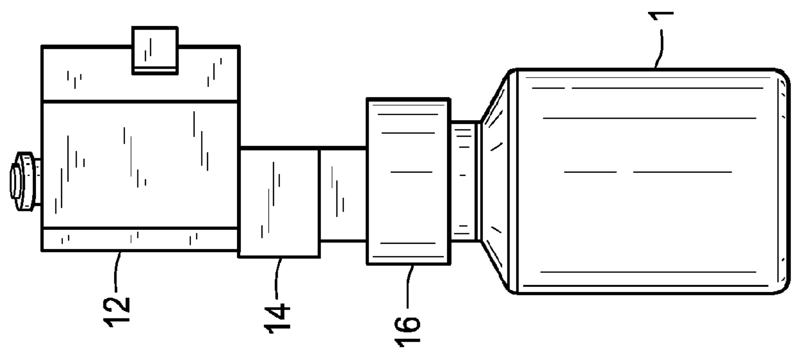
FIG. 5 depicts a side elevational view of the piercing device of FIG. 1.

Needle holder 12 includes an upper housing 12' which receives hubs 26 and 28 and a lower housing 12" through which needles 18 and 20 extend. The upper portion 12' of needle holder 12 includes two portions 12*a* and 12*b* connected at a flexible hinge 13. Portions 12*a* and 12*b* include cooperating apertures 21 and 23 through which hubs 26 and 28 extend in their deflected orientation. The lower portion 12" of needle holder 12 engages needles 18 and 20. Portion 12*b* supports a latch means 15 for engaging coplanar surface 17, when portions 12*a* and 12*b* are brought together, on portion 12*a*. Device 10 is thus able to enclose the needle hubs therein and hold them in the deflected orientation. The present invention contemplates that portions 12*a* and 12*b* could be formed as solid blocks with cooperating receptacles formed therein for receiving and holding hubs 26 and 28 in their deflected orientation with respect to needles 18 and 20. Alternatively, portions 12*a* and 12*b* could be formed as two-halves of an enclosing box which snap together to hold hubs 26 and 28 in their deflected orientation. Alternatively still, and as shown in FIGS. 1 and 2, portion 12*a* may be formed as a solid block having the negative of a portion of hubs 26 and 28 formed therein while portion 12*b* is formed as a box having a perimetrical wall defining a cavity 11 for accommodating hubs 26 and 28.

Piercing guide 14 and vial collar 16 may be formed either as separate components which are mated together, or as a single component which provides both functions. When formed as separate components, the present invention contemplates both piercing guide 14 and vial collar 16 may be removable from container 1 so that, after filling, container 1 will be free of all components of the present invention. Alternatively, vial collar 16 may remain with container 1 after needle holder 12 and guide 14 is removed therefrom. Vial collar 16 may thus be removably snapped into position about neck 4 of container 1 by deflection of vial collar 16. Similarly, when piercing guide 14 is not affixed to vial collar 16, piercing guide may be removably attached thereto by means such as an interference fit, a bayonet-type connection, threaded connection, etc. Desirably, the present invention contemplates that needle holder 12 will be affixed to piercing guide 14 once moved to the second position so that needle holder 12 would be removed from container with piercing guide 14, whether with vial collar 16 or not. That is, the present invention contemplates that it will be far easier to remove either piercing guide 14 from vial collar 16 or vial collar 16 from the neck of the container than to remove needle holder 12 from piercing guide 14.

Figure 7:
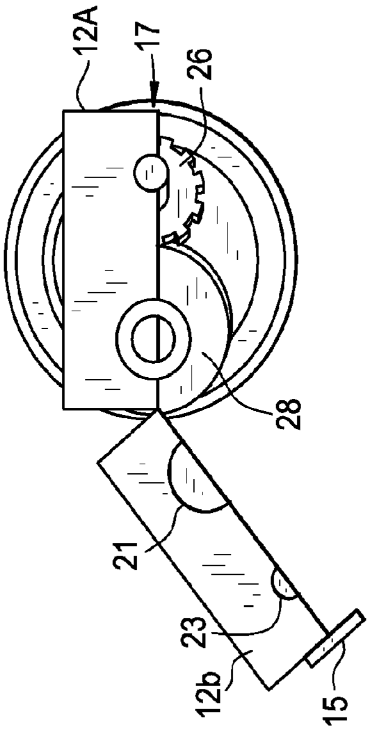
FIG. 7 depicts a top view of the piercing device of FIG. 1.
Figure 8:
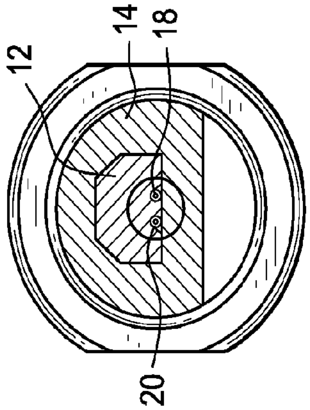
FIG. 8 depicts a cross-sectional view of the piercing device of FIG. 2, taken through the line 8-8.
Figure 9:
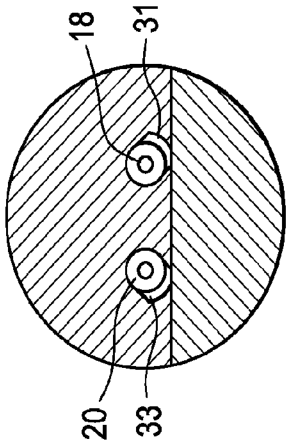
FIG. 9 is a detail view of the center portion of FIG. 8.

FIG. 7 is a top-view of needle holder 12 showing panel 12*b* in the open position. FIG. 8 depicts a cross-sectional view through the upper portion of guide 14. FIG. 9, depicts the central portion of FIG. 8 and shows that lower portion 12" includes open channels 31 and 33 therethrough for receiving needles 18 and 20, respectively. Channels 31 and 33 are each defined by elongate channel walls and may be larger in cross-section than needles 18 and 20 so as to accommodate the flexing of the needles when bent to fit within device 10. Desirably, channels 31 and 33 have a tapering shape so as to converge about each of needles 18 and 20, respectively, so that the ends 18*a* and 20*a* are substantially-embraced by the channel walls. The present invention contemplates, however, that the channel walls engage their respective needle from opposing directions adjacent free end of the needle and its respective hub so as to assist, with additional deflection provided by upper portion 12', in imparting the bend in accordance with the present invention.

Figure 10:
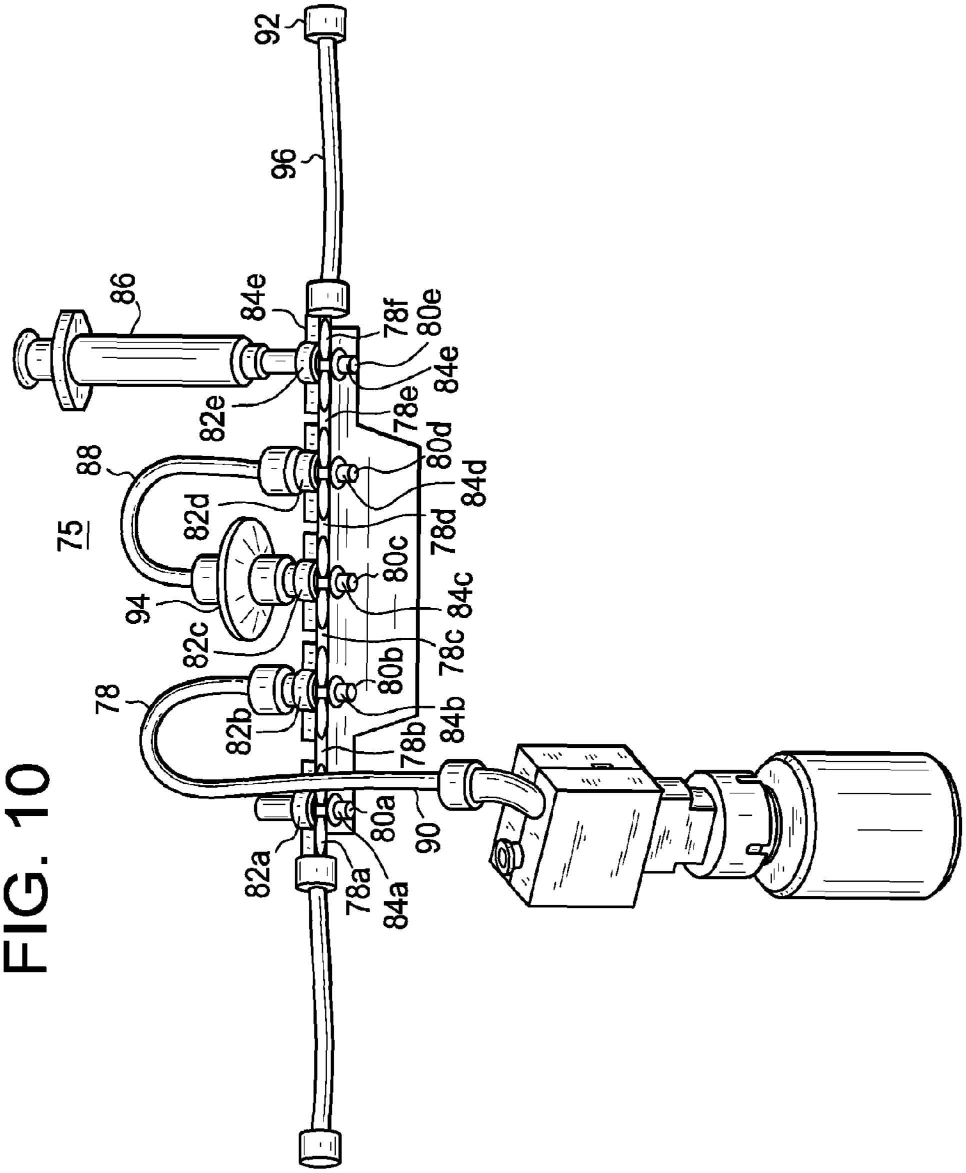
FIG. 10 depicts a dispense cassette incorporating a piercing device of the present invention.

Referring now to FIG. 10, the present invention contemplates that piercing device 10 may be incorporated into a dispense cassette 75 for container 1. Dispense cassette 75 includes a manifold body 76 defining co-axially aligned passageway segments 78*a-f* of a passageway 78, a number of valve sockets 80*a-e* along passageway 78, each valve socket in fluid communication with both flowpath 78 and a unique conduit 82*a-e*, also defined by manifold body 76. A valve 84*a-e* is positioned in each valve socket 80*a-e*, respectively. Dispense system further includes a syringe pump 86 positioned in sealed fluid communication with conduit 82*e*, a filter conduit 88 extending in sealed fluid communication between conduits 82*c-d*, and a dispense conduit 90 extending to piercing device 10, all for directing flow from a source input 92 to a container 1. Filter conduit 88 supports a filter 94 thereon. Filter 94 is desirably a dead-end filter which filters a source fluid from conduit 80*d* into a cleaner filtrate flowing into conduit 82*c*. A dead-end filter is sufficient when dispense cassette 75 is used as a single-use system and even for most dispenses should it be re-used. Filter 94 desirably provides a 0.22 micron filter although the filter specifications may be selected as desired for the particular operation. Dispense cassette 75 thus provides a feed flowpath 96 through which a source fluid flows from an exterior fluid source to filter 94. Dispense cassette 75 also provides a filtrate flowpath 78 leading from filter 94 to at least one product dispense vial 1. Feed flowpath 96 comprises passageway segment 78*f*, conduit 80*e*, syringe pump 86, passageway segment 78*e*, conduit 80*d*, and filter conduit 88. Filtrate flowpath 78 extends from filter 94 through conduit 82*d*, segment 78*c*, conduit 82*c*, and dispense conduit 90. Feed flowpath 96 is thus in filtered fluid communication with filtrate flowpath 78 through filter 94.

Dispense conduit 90 connects to fill needle 18 supported in needle holder 12 of piercing device 10. When needle holder 12 is moved into the second position, filtrate flowpath 78 will be in sealed fluid communication with cavity 3 of container 1. Vent needle 20 is also supported by needle holder 12 such that a first end will pierce into cavity 3 while the second end will be in sealed fluid communication with another filter 100 which would thus maintain the sterile integrity of cavity 3 and filtrate flowpath 98. The vent filter allows any entrapped gas within cavity 3 to escape while still maintaining the product filtrate fluid within container 1. Vent needle 20 typically includes an elongate hollow vent conduit body supporting a filtration media therein, or in sealed fluid communication therewith, for allowing air to vent from cavity 3 while maintaining the controlled environment thereof. It is further contemplated by the present invention that filters may also be positioned at each end of manifold body 76 so as to maintain the sterile integrity of all flowpaths and passageways of dispense cassette 75. In this manner, dispense cassette 75 may be connected together in an environmentally-controlled environment, desirably a sterile or a GMP-compliant environment, so that all of the fluid flowspace beyond filter 94 continues to meet the standards of the controlled environment. Desirably, a Class A environment is provided and maintained by the present invention. When dispense cassette 75 is manufactured in such a sterile manner, it may be placed into and sealed within the containment cavity 104 of a containment bag 102 so as to maintain the sterility of at least dispense flowpath 78. Additionally, the present invention contemplates that piercing device 10 may be included in bag 102 with both fill needle 18 and vent needle 20 held by needle holder 12 in the first position.

An operator may then manipulate piercing device 10 through bag 102, prior to the containment bag 102 being opened, so that needle holder 12 will be in the second position and thus allow dispensing into container 1. The septum 7 of container 1 may thus be pierced shortly before dispense system is removed from bag 102 and used to fill container 1, thereby minimizing the time that septum 7 is pierced prior to filling.

Syringe pump 86 may be manually, electrically or pneumatically controlled to draw a source fluid from a source connected at source input 92 and to then expel the source fluid back out. Valve 84*e* provides selectable fluid communication between pump 86 and either source input 92 or passageway segment 78*f* and thus filter 94.

The present invention thus also provides a kit for dispensing radiopharmaceuticals. The kit of the present invention includes a container including a container body defining a container cavity and a container aperture in fluid communication with the container cavity. The container aperture is sealed by an elastomeric septum positioned thereover. The kit provides a dispense manifold including a manifold body defining an elongate fluid conduit, a filter at one end of the conduit, and at least one valve located along the fluid conduit for selectably directing a fluid in the fluid conduit toward a first or second dispense conduit. Each of the first and second dispense conduits support a respective one of a first and second fill needle affixed to the end thereof. The kit further includes a connector cap of the present invention for each of the dispense conduits extending from the manifold. Each of the dispense needles is held by the needle holder of its respective connector cap in the first position, and the vial collar of each connector cap is affixed about a vial such that the collar aperture is in overlying registry with the septum sealing its respective vial. The dispense manifold and connector caps and vials are adapted to be held within the container cavity such that each connector cap is moveable from the first position to the second position while in the container. The container desirably maintains a sterile environment therein while sealed and may be a plastic bag and may further include a plastic tray formed to hold the manifold and each connector cap and vial. The tray may further comprise a deflectable blister adjacent to each needle holder so as to move the needle holder from the first to the second position when the blister is deflected. The manifold may further include a pump mechanism for directing a fluid through the filter, through said fluid conduit, and into a vial.

Dispense cassette 75 is desirably operated by a PLC controller (not shown) for selectively operating syringe pump 86 and valves 84*e-f* so as to direct fluid from fluid source 92 to container 1. For convenience, associated electrical connections from the controller are not shown. Thus, dispense cassette 75 may include connectors for mating with an exterior controller or hardware platform which provides appropriate actuation of the pump and valve elements thereof.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A connector cap for a vial sealed by an elastomeric septum, said connector cap comprising:

a vial collar comprising a vial collar body defining a collar aperture to be positioned in overlying registry with the septum of the vial, and a needle holder comprising a needle holder body having a first portion providing a means for engaging the first end of an elongate needle in registry with the collar aperture and a second portion for securing an opposed second end of the needle, said needle holder body being moveable with respect to said vial collar between a first position spaced from said vial collar and a second position proximate said vial collar, such that the free end of the first portion of a needle held by said needle holder will puncture through the vial septum, wherein said first and second portions of said needle holder body cause a needle held thereby to be bent between the first and second ends of the needle.

2. A connector cap of claim 1, wherein said collar body further comprises an annular guide body defining a guide cavity in fluid communication with said collar aperture, said needle holder, said guide body receiving said first portion of said needle holder there at both said first and second positions.

3. A connector cap of claim 2, wherein said clamp mechanism further comprises an opposing clamp base and clamp arm such that the clamp arm is movable towards said clamp base so as to secure the second end of the needle.

4. A connector cap of claim 3, wherein said clamp base includes a clamp base body which defines a channel into which at least a portion of the needle may be positioned.

5. A connector cap of claim 4, wherein said clamp base body further comprises a planar clamp base surface defining said channel.

6. A connector cap of claim 5, wherein said channel is further sized and shaped to accommodate at least a portion of one of a filter or a luer connector connected at the second end of the needle.

7. A connector cap of claim 3, wherein said clamp arm and said clamp base may be fixedly connected with the needle therebetween.

8. A connector cap of claim 3, wherein said clamp arm and said clamp base are disconnectably connected to each other with a needle therebetween.

9. A connector cap of claim 1, wherein said first portion of said needle holder further comprises an elongate body defining opposed first inlet and first exit apertures and an elongate first needle passageway extending in fluid communication therebetween.

10. A connector cap of claim 9, wherein said first portion of said needle holder further comprises an elongate body defining opposed second inlet and second exit apertures and an elongate second needle passageway extending in fluid communication therebetween, said second needle passageway transversely spaced from said first needle passageway.

11. A connector cap of claim 10, wherein said exit apertures of said first portion of said needle holder are centrally positioned within said vial collar.

12. A connector cap of claim 1, wherein said vial collar is removably attachable to the vial.

13. A connector cap of claim 1, further comprising a locking mechanism for maintaining said needle holder in said first position with respect to said vial collar.

14. A kit for dispensing radiopharmaceuticals, said kit comprising:

- a container including a container body defining a container cavity and a container aperture in fluid communication with said container cavity, said container aperture sealed by an elastomeric septum positioned thereover;
- a dispense manifold comprising a manifold body defining an elongate fluid conduit, a filter at one end of said conduit, at least one valve located along said fluid conduit for selectably directing a fluid in said fluid conduit toward a first or second dispense conduit, each said first and second dispense conduit supporting a respective one of a first and second fill needle affixed to the end thereof;
- a connector cap of claim 1 for each said dispense conduit extending from said manifold, wherein each said needle is held by the needle holder of its respective connector cap in the first position, and wherein the vial collar of each said connector cap is affixed about a vial such that the collar aperture is in overlying registry with the septum sealing its respective vial;
- wherein said dispense manifold and each said connector cap and vial are adapted to be held within the container cavity and wherein each said connector cap is moveable from said first position to said second position while in said container.

15. A kit of claim 14, wherein said container is a plastic bag.

16. A kit of claim 14, wherein said container further comprise a plastic tray formed to hold the manifold and each connector cap and vial.

17. A kit of claim 14, wherein said manifold further comprises a pump mechanism for directing a fluid through the filter, through said fluid conduit, and into a vial.

18. A kit of claim 14, wherein said container cavity maintains a sterile environment therein while sealed.

19. A method of positioning a pair of needles in registry with an elastomeric septum spanning the aperture of a vial, comprising the steps of:

- Providing a connector cap of claim 1,
- Inserting a first elongate needle having opposed first and second ends, the second end supporting a luer connector thereon, into the needle holder of the connector cap by the steps comprising:
- Inserting the first end of the needle through the first needle passageway such that the free end of the first end of the needle projects from the exit aperture;
- Bending the first needle such that the second end of the needle is deflected radially-outward from the elongate axis of the first portion of the needle holder body to a deflected orientation;
- Inserting a second elongate needle having opposed first and second ends, the second end supporting a luer connector thereon, into the needle holder of the connector cap by the steps comprising:
- Inserting the first end of the second needle through the second needle passageway such that the free end of the first end of the second needle projects from the second exit aperture;
- Bending the second needle such that the second end of the second needle is deflected away from said second end of said first needle to a deflected orientation; and
- Clamping the second ends of the first and second needle in their respective deflected orientation.

20. A method of claim 19, wherein said clamping step further comprises the steps of:

- Moving clamp arm to the clamped position; and
- Securing said clamp arm in the clamped position.

* * * * *